US008691586B2

(12) United States Patent  (10) Patent No.: US 8,691,586 B2
Bayley et al.  (45) Date of Patent: Apr. 8, 2014

(54) FORMATION OF BILAYERS OF AMPHIPATHIC MOLECULES

(75) Inventors: John Hagen Pryce Bayley, Oxford (GB); Matthew Holden, Oxford (GB); Andrew John Heron, Oxford (GB); David Needham, Durham, NC (US)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 13/607,337

(22) Filed: Sep. 7, 2012

(65) Prior Publication Data

US 2013/0146815 A1 Jun. 13, 2013

Related U.S. Application Data

(63) Continuation of application No. 12/375,103, filed as application No. PCT/GB2007/002856 on Jul. 26, 2007, now Pat. No. 8,268,627.

(30) Foreign Application Priority Data

Jul. 26, 2006 (GB) .................................. 0614835.7

(51) Int. Cl.
  *G01N 33/68* (2006.01)
(52) U.S. Cl.
  USPC .............................................. 436/71; 436/55
(58) Field of Classification Search
  USPC ...................................................... 436/71, 55
  See application file for complete search history.

(56) References Cited

U.S. PATENT DOCUMENTS

| 6,962,747 B1 | 11/2005 | Sasaki et al. |
| 2009/0012187 A1 | 1/2009 | Chu et al. |
| 2010/0147450 A1 | 6/2010 | Takeuchi et al. |

FOREIGN PATENT DOCUMENTS

| EP | 1712909 | 10/2006 |
| JP | 3-118832 | 5/1991 |
| JP | 2006-312141 | 11/2006 |
| JP | 2007-29911 | 2/2007 |
| WO | WO 2007/013493 | 2/2007 |

OTHER PUBLICATIONS

International Search Report for PCT/GB2007//002856, mailed Nov. 8, 2007.
Written Opinion of the International Searching Authority for PCT/GB2007/002856, mailed Nov. 8, 2007.
Noireaux et al., "Toward an Artificial Cell Based on Gene Expression in Vesicles", Physical Biology, Sep. 2005, vol. 2, No. 3, pp. P1-P8, XP002456395.
Suzuki et al., "Planar Lipid Bilayer Reconstitution with a Micro-Fluidic System", Lab on a Chip, Oct. 2004, vol. 4, No. 5, pp. 502-505, XP008085264.

(Continued)

*Primary Examiner* — Monique Cole
(74) *Attorney, Agent, or Firm* — Nixon & Vanderhye P.C.

(57) ABSTRACT

A method of forming bilayers of amphipathic molecules uses droplets of aqueous solution in a hydrophobic medium such as oil. A layer of amphipathic molecules such as a lipid is formed around the surfaces of the droplets. This may be achieved by providing the lipid in the oil and leaving the droplets for a time sufficient to form the layer. The droplets are brought into contact with one another so that a bilayer of the amphipathic molecules is formed as an interface between the contacting droplets. The bilayers may be used for a wide range of studies. The technique has numerous advantages including providing a long lifetime for the bilayers, allowing study of small volumes and allowing the construction of chains and networks of droplets with bilayers in between to study complex systems.

24 Claims, 5 Drawing Sheets

(56) References Cited

OTHER PUBLICATIONS

Holden et al. "Functional Bionetworks from Nanoliter Water Droplets", J. AM. Chem. Soc.; Journal of the American Chemical Society, Jul. 11 2007, vol. 129, No. 27, pp. 8650-8655, XP002456396.

Funakoshi et al., "Lipid Bilayer Formation by Contacting Monolayers in a Microfluidic Device for Membrane Protein Analysis." Analytical Chemistry, vol. 78, No. 24, Dec. 15, 2006, pp. 8169-8174, XP002456397.

Funakoshi et al, "Ultra Giant Vesicles out of a Planar membrane", Proceedings of 2006 International Conference on Microtechnologies in Medicine and Biology, Okinawa, Japan, May 9-12, 2006.

Funakoshi et al, "Vesicle Formation by Micro Pulse Jet", IEEJ Research Paper, Japan Institute of Electrical Engineers of Japan (IEEJ), pp. 9-12 (2006).

Suzuki et al, "Highly Reproducible Method of Planar Lipid Bilayer Reconstitution in Polymethacrylate Micofluidic Chip", Langmuir 22:1937-1942 (2006).

Bibette et al, "Emulsions: basic principles" Rep. Prog. Phys. 62 (1999) 969-1033.

Jorgensen et al, "Micropipette Manipulation: A Technique to Evaluate the Stability of Water-in-Oil Emulsions Containing Proteins", Journal of Pharmaceutical Sciences, vol. 93, No. 12, Dec. 2004.

Poulin et al, "Adhesion between Pure and Mixed Surfactant Layers", Langmuir 1999, 15, 4731-4739.

Pringen, "Geometry of Clusters of Strongly Coagulated Fluid Drops and the Occurrence of Collapsed Plateau Borders", Colloids and Surfaces, 9 (1984) 47-66.

Tsofina et al, "Production of Bimolecular Protein-Lipid Membranes in Aqueous Solution", Nature, Nov. 12, 1966, pp. 681-683.

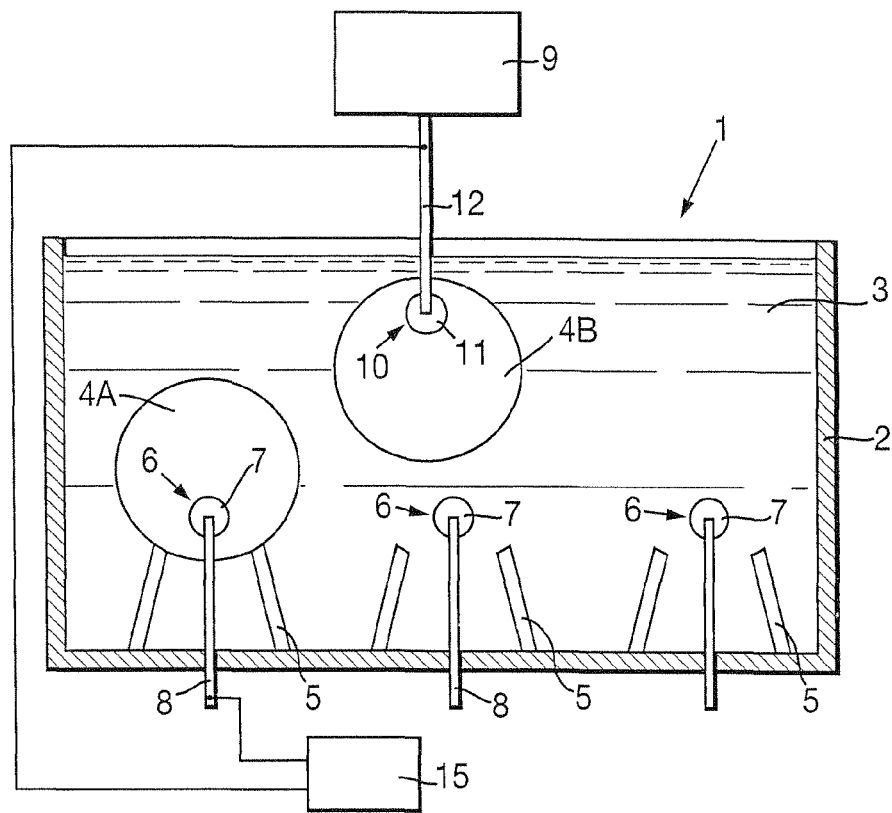
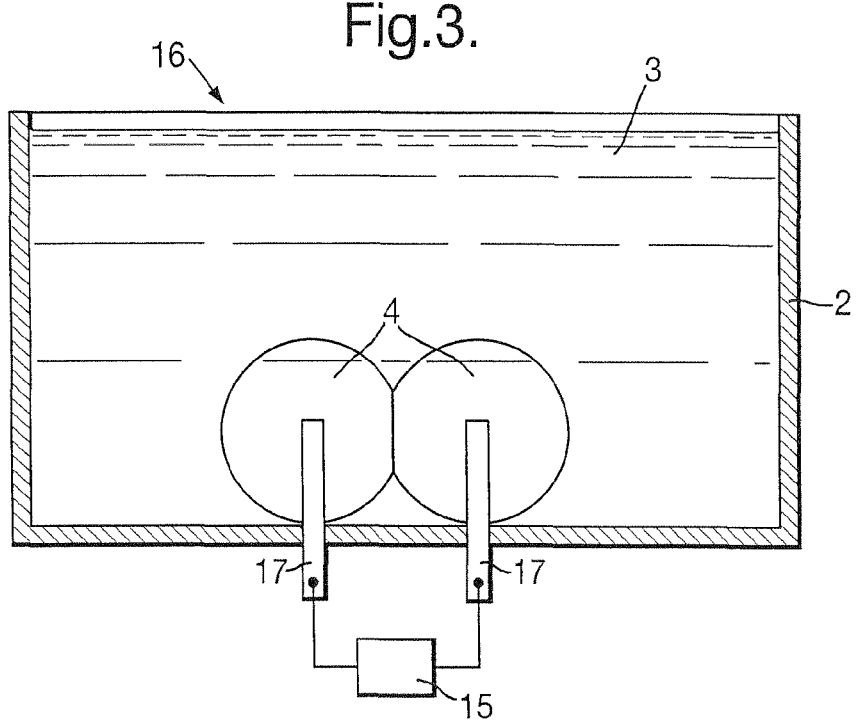

FORMATION OF BILAYERS OF AMPHIPATHIC MOLECULES

This application is a continuation of U.S. application Ser. No. 12/375,103, filed Sep. 9, 2009 now U.S. Pat. No. 8,268,627, which is the U.S. national phase of International Application No. PCT/GB2007/002856, filed Jul. 26, 2007, which designated the U.S. and claims priority to Great Britain Application No. 0614835.7, filed Jul. 26, 2006, the entire contents of each of which are hereby incorporated by reference.

This invention was made with government support under Grant No. FA9550-06-C-0006 awarded by USAF/AFOSR. The government has certain rights in this invention.

The present invention relates to the formation of bilayers of amphipathic molecules such as lipids. Such bilayers are models of cell membranes and as such may be used to perform a wide range of studies in biotechnology.

Lipid bilayers, or more generally bilayers of amphipathic molecules, are models of cell membranes and serve as excellent platforms for a range of experimental studies, for example in vitro investigation of membrane proteins by single-channel recording. Conditions such as temperature, bilayer composition (surface charge, cholesterol content etc.) and transmembrane potential can be adjusted to either mimic biological systems or venture beyond the physiological range. Most importantly, manipulation of the solution conditions (pH, salt composition, ionic strength) is possible on both sides of the membrane. While the in vivo investigation of membrane proteins in living cells is possible by the patch clamp method, the conditions that can be used are limited by the requirement to keep the cells healthy.

In the conventional technique, planar lipid bilayers are formed over a plastic aperture which has been pretreated with an oily mixture. Despite widespread use in academic research, this conventional technique suffers from a number of limitations, for example as follows.

The conventional technique is cumbersome and the bilayers produced are delicate. The two most common methods of forming planar bilayers are to paint a lipid/oil mixture across an aperture and to fold together two monolayers, one from each side of an aperture. Both techniques require the hands of a skilled scientist. Small hydrostatic forces due to vibration or flow often rupture planar bilayers. Even under the best conditions, the lifetime of a planar bilayer is usually only a few hours. The limited lifetime effectively limits the range of processes which it is possible to study.

Also, since the size and shape of the each bilayer's annulus region (which governs the membrane's properties) is unique, the insertion of membrane proteins into planar bilayers is difficult to standardize.

Another cause of difficulty when studying some systems is that the volume of the electrical recording cell on either side of the planar bilayer is typically greater than 1 mL. Therefore, each experiment needs large amounts of protein or other reagents, which may not be easy to produce. After each experiment, both sides of the electrical recording cell must be thoroughly cleaned.

Lastly, the conventional technique uses a single planar bilayer between two chambers. To study systems comprising larger numbers of membranes, it would in principle be possible to construct a cell having more chambers and membranes, but the experimental techniques of forming the bilayers would be very complicated and in practical terms would make this very laborious and unattractive to the scientist.

It would be desirable to develop an alternative method which alleviates one or more of these limitations.

According to the present invention, there is provided a method of forming bilayers of amphipathic molecules, comprising:

forming a plurality of droplets of aqueous solution in a hydrophobic medium with a layer of amphipathic molecules around the surfaces of the droplets;

bringing droplets into contact with one another so that a bilayer of the amphipathic molecules is formed as an interface between contacting droplets.

This method of forming bilayers has considerable advantages and in particular overcomes the limitations of the conventional technique discussed above.

The method is straightforward to perform and results in robust bilayers which can be used in a wide range of studies and applications in the field of biotechnology. The droplets can be formed very easily, for example simply by pipetting aqueous solution into the hydrophobic medium. Similarly, the droplets are easily moved around to bring them into contact with each other. Indeed the manner in which droplets are moved is not critical as the droplets are robust and easily manipulated. Examples of suitable apparatus for handling the droplets are given below, but are not limitative.

The formation of a layer of amphipathic molecules around the surfaces of the droplets is also straightforward. For example, it may be achieved simply by providing the amphipathic molecules in the hydrophobic medium or in the aqueous solution of the droplets, whereupon the layer can form naturally if the droplets are left for a sufficient period of time. The amphipathic molecules may also be dissolved, or suspended as lipid vesicles in the droplets themselves, from where they again spontaneously form monomolecular layers at the interface between the droplet and the hydrophobic medium, that may have an equilibrating concentration of the amphipathic molecule in the hydrophobic medium.

The bilayer is formed simply by bringing droplets into contact with one another. The orientation of the amphipathic molecules in the layer around the aqueous solution allows the formation of the bilayer. As the droplets are brought into contact, after the intervening hydrophobic medium has been displaced the bilayer forms very quickly as an interface between the contacting droplets. The bilayer forms a planar surface between the two droplets which are otherwise generally spherical. This planar bilayer is the shape with the lowest free surface energy and has a negative free energy of formation; it is therefore a spontaneous event. The amphipathic molecules allow two droplets to be brought into contact without allowing them to coalesce by the formation of a stable bilayer.

The droplets may be handled by a variety of techniques. One particularly advantageous method of moving the droplets is to dispose an anchor having a hydrophilic outer surface inside a droplet. Movement of the allows the droplet to be moved, for example to bring it into contact with another droplet.

The bilayer can be used to perform experiments involving a process occurring at or through the bilayer of the amphipathic molecules. A major class of experiments use a membrane protein inserted into the bilayer. This may be achieved simply by providing the membrane protein in the aqueous solution. It has been shown that after the formation of the bilayer, the membrane protein naturally inserts into the bilayer in the same manner as with a bilayer formed by the conventional technique.

It has been observed that the bilayer behaves functionally in the same manner as a bilayer formed by the conventional technique. Therefore the bilayer formed by the present method can be used to perform the same types of experiments, but providing a number of advantages which broaden the range of possible experiments, as discussed further below. Thus the present method may be applied to a wide range of experiments including investigation and/or screening of membrane proteins, investigation and/or screening of analytes which interact with membrane proteins, and investigation and/or screening of the bilayers. Indeed the method may be used to study any bilayer phenomena in general, typically involving a process occurring at or through the bilayer.

The lipid bilayer may also be used to study the properties of the membrane protein inserted therein. For example, the voltage dependence of the properties of the membrane protein may be determined Techniques for studying membrane proteins in lipid bilayers are well known in the art. The function of a channel or pore may be determined by measuring, for example, an ionic current flowing across the lipid bilayer through a membrane protein. The function of a transporter may be determined by measuring the amount of a molecule translocated across the lipid bilayer, for example by mass spectrometer or ELISA or by using a substrate which is tagged fluorescently or radioactively.

Other examples of experiments which may be performed as follows.

The water droplets can be osmotically inflated or deflated depending on their initial osmolarity. Water can transfer between the droplets in response to an osmotic gradient through the formed bilayer at the contact. Also, other molecules that are bilayer permeable, like drugs, or imageable molecules can be made to move from one droplet to another through the bilayer contact zone. Thus, reactants can be separated and allowed to react only when transported across the bilayer. Here applications may involve microfluidic systems of droplets that can be brought into contact and allowed to react to produce new products formed only when the reactants cross the bilayer contacts between different droplets. One possibility is that one reactant is bilayer permeable while the other is not bilayer permeable. In this case the products only occur in the droplet containing the non-bilayer permeable reactant. If on the other hand both reactants are bilayer transferable then the products can be formed in both droplets, or a plurality of contacting droplets, dependent on the relative permeability of each reactant across the contact bilayers. These examples do not involve membrane proteins per se, but just the formed bilayer contacts through which reactants and products might diffuse.

Further specific examples of studies to which the present method may be applied are discussed further below.

In many studies electrical measurements are taken. This is straightforward to achieve by bringing electrodes into electrical contact with the droplets when the droplets are in contact with one another, for example by insertion of the electrodes into the droplets or by placing droplets onto static electrodes inserted into the chamber or in the microfluidic channels Bilayers formed by the present method have the advantage of being robust and having a long lifetime, as compared to the conventional technique. For example bilayers formed by the conventional technique require skill to prepare and typically last a few hours and at most in a very small percentage of cases a couple of days. In contrast bilayers formed by the present technique are formed more reliably and last much longer, generally lasting a number of days. Although a full study of lifetime has not been performed, a bilayer has been observed to last for a period of 8 days before it was purposely divided by separating the drops.

It is hypothesised that the reason for the higher lifetime is that the bilayer formed between two droplets has a lower surface free energy than a bilayer formed by the conventional technique. In the latter case, in the annulus region adjacent the periphery of the aperture, the bilayer divides into two monolayers which extend on opposite sides of the barrier defining the aperture. It may also be that stability is conferred by the absence of an annulus that has to be attached (or adsorbed) onto the material of a septum defining an aperture. In a similar fashion to the conventional technique, the bilayer also divides into two monolayers which in this case simply coat the droplet interfaces, and do not terminate at a support material (except at the surface of the chamber). The bilayer is therefore not "stretched" across an aperture, but forms at the contact zone of the two droplets and no additional spreading or wetting tensions are induced, just the bilayer tension determined by the monolayer tension and the free energy of formation in the hydrophobic medium.

The higher lifetime allows the study of biological processes which themselves have a longer lifetime. In this way the present method opens up new fields of study.

The formation of the bilayers is also highly reversible and repeatable. Droplets which have been brought into contact with one another may be freely separated to divide the bilayer and may be subsequently brought into contact again to re-create the bilayer. Such control over the creation, division and re-creation of bilayers also opens up new fields of study.

The degree of control makes the formation of the bilayers easy to standardise. In particular, it is easy to vary the area of the bilayer of the amphipathic molecules by moving the droplets when the droplets are in contact with one another. The change in the area of the bilayers may be observed visually or by capacitance measurements. It has been demonstrated that it is possible to change the diameter of the bilayer over the range from 30 µm to 1000 µm, although this is not thought to be the limit.

In addition, the nature of the hydrophobic medium determines the degree of spreading of the contacted monolayers and thereby the contact angle. For example, in experiments it has been observed that for bilayers of glycerylmonooleate (GMO) formed in decane as the hydrophobic medium, the contact area is relatively small and the contact angle is about 3°, this being in agreement with contact angles measured in conventional lipid membrane systems. On the other hand, if the hydrophobic medium is squalene, a larger contact area is formed and the contact angle is 25°, again in agreement with measurements on conventional lipid membranes. These solvent-dependent effects reflect the small free energy of formation of the GMO:decane system (around −4 mJ/m$^2$) as compared to the GMO:squalene system (around −500 mJ/m$^2$), where the bilayer thickness concomitantly decreased from 50 Å to 25 Å, signifying a depletion of the larger squalene solvent from the bilayer. This non-linear increase in free energy of formation departs from simple Lifshitz theory for two infinite slabs of water acting across the thin oil film, and is more in line with a "depletion flocculation" effect. Essentially, the larger squalene solvent molecules are entropically excluded from the GMO bilayer, and this depletion of solvent exerts a greater osmotic pressure on the bilayer, thereby raising the free energy of formation by orders of magnitude in going from decane to squalene, over and above any Lifshitz effects. Adhesion and the strength and stability of the contact then are largely dependent on the presence or absence of solvent in the bilayer.

Another advantage of the present method is that it allows the use of a relatively small volume of aqueous solution. In particular, the volume may be smaller than that present in the chambers of a cell used in the conventional technique. The droplets may typically have a volume less than 1000 nL. In general the droplets may be of any size limited only by the degree of control of the dispenser of the aqueous solution and the limits of optical resolution if direct manipulation is desired. Droplets that are not required to have electrical recording or stimulus from placed electrodes can be assembled in suspension forming a raft or 3D aggregate or flocculent of droplets having dimensions of micrometers to even nanometers that are all in contact with each other via their intervening bilayers. Using a standard pipette, experiments have been performed on droplets having volumes in the range from 200 nL to 800 nL but it is expected that droplets of smaller volumes could be produced with suitable equipment. For example, using micro-pipette manipulation to form the droplets from glass micro-pipettes observed in a relatively powerful microscope, where droplets of diameter say 30 µm are assembled, the volume is approximately 14 pL. In suspension, droplet aggregation of droplets of diameter say 200 nm yields internal volumes of approximately 4 aL (aL stands for attoliter being $10^{-18}$ L).

An important advantage of the present invention is that it is possible to bring more than two droplets into contact with each other in a chain or network, for example on a flat or dimpled surface, in a microfluidic channel or, as alluded to above, in aggregated or flocculated suspension. The simplicity and control with which the bilayers can be formed simply by moving droplets around makes it straightforward to build large chains or networks which would be impractical in a system where bilayers are formed in apertures in barriers in accordance with the conventional technique. This opens up the possibility of studying much larger systems than is practical with the conventional technique, for example modelling entire systems using multiple droplets. Some examples are given below, but the range of science which could be studied is much wider.

The method can be performed with a wide range of materials, as follows.

In general, the amphipathic molecules can be of any type which form a bilayer in the hydrophobic medium in which the droplets are positioned. This is dependent on the nature of the hydrophobic medium and the aqueous solution, but a wide range of amphipathic molecules are possible. Amphipathic molecules are molecules which have both hydrophobic and hydrophilic groups. The layer formed around the droplet is a monolayer of amphipathic molecules which is formed and maintained naturally by the interaction of the hydrophobic and hydrophilic groups with the aqueous solution so that the molecules align on the surface of the droplet with the hydrophilic groups facing inwards and the hydrophobic groups facing outwards.

An important class of amphipathic molecules to which the present method may be applied is lipid molecules. The lipid molecules may be any of the major classes of lipid, including fatty acyls, glycerolipids, glycerophospholipids, sphingolipids, sterol lipids, prenol lipids, saccharolipids and polyketides. Some important examples include a phospholipid, a glycolipid or cholesterol. The lipid molecules may be naturally occurring or synthetic. Whilst the formation of a bilayer from lipid molecules has been demonstrated the method is expected to be appropriate for any amphipathic molecules capable of forming a bilayer.

The amphipathic molecules need not be all of the same type. The amphipathic molecules may be mixtures. Another important example is that the amphipathic molecules in the respective layers of two droplets brought into contact are of different types so that the bilayer formed by the two monolayers is asymmetric.

The aqueous solution may be freely chosen for the experimental study which is to be performed. The aqueous solution of each droplet may be the same or different. The nature and concentration of the solutes can be freely varied to vary the properties of the solution. One important property is pH and this can be varied over a wide range. Another important point in experiments using electrical measurements is to select appropriate salts to carry the current. Another important property is osmolarity.

The hydrophobic medium can also be selected from a wide range of materials. The material is hydrophobic so that the aqueous solution forms a droplet rather than mixing with the hydrophobic medium but otherwise the hydrophobic medium can be freely chosen. The viscosity of the hydrophobic medium can be selected to affect the movement of the droplets and the speed of formation of the layer of amphipathic molecules in the case that they are provided in the hydrophobic medium.

The hydrophobic medium may be an oil. Any type of oil is suitable as long as its surface activity is relatively high, and that it does not destabilize the formed bilayers. The oil may be a hydrocarbon which may be branched or unbranched, for example a hydrocarbon having from 5 to 20 carbon atoms (although hydrocarbons of lower molecule weight would require control of evaporation). Suitable examples include alkanes or alkenes, such as hexadecane, decane, pentane or squalene. Other types of oil are possible. For example the oil may be a fluorocarbon. This might be useful for the study of some systems, for example to minimise loss of a particular membrane protein or analyte from the droplet or to control gas content such as oxygen.

As discussed above, in many experimental studies a membrane protein is provided in one or more of the droplets for insertion into the bilayer. The present method does not limit the choice of membrane protein, provided that the aqueous solution is chosen with appropriate properties for the protein in question. Thus the membrane protein may be of any type. The use of integral membrane proteins has been demonstrated, but it is equally expected that peripheral membrane proteins could be used. The present method applies to any membrane proteins including the two major classes that is β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction.

To allow better understanding, embodiments of the present invention will now be described by way of non-limitative example with reference to the accompanying drawings, in which:

FIG. 1 is a cross-sectional view of an apparatus for handling droplets to form a bilayer;

FIG. 3 is a cross-sectional view of an alternative apparatus for handling droplets to form a bilayer;

Figure 2:
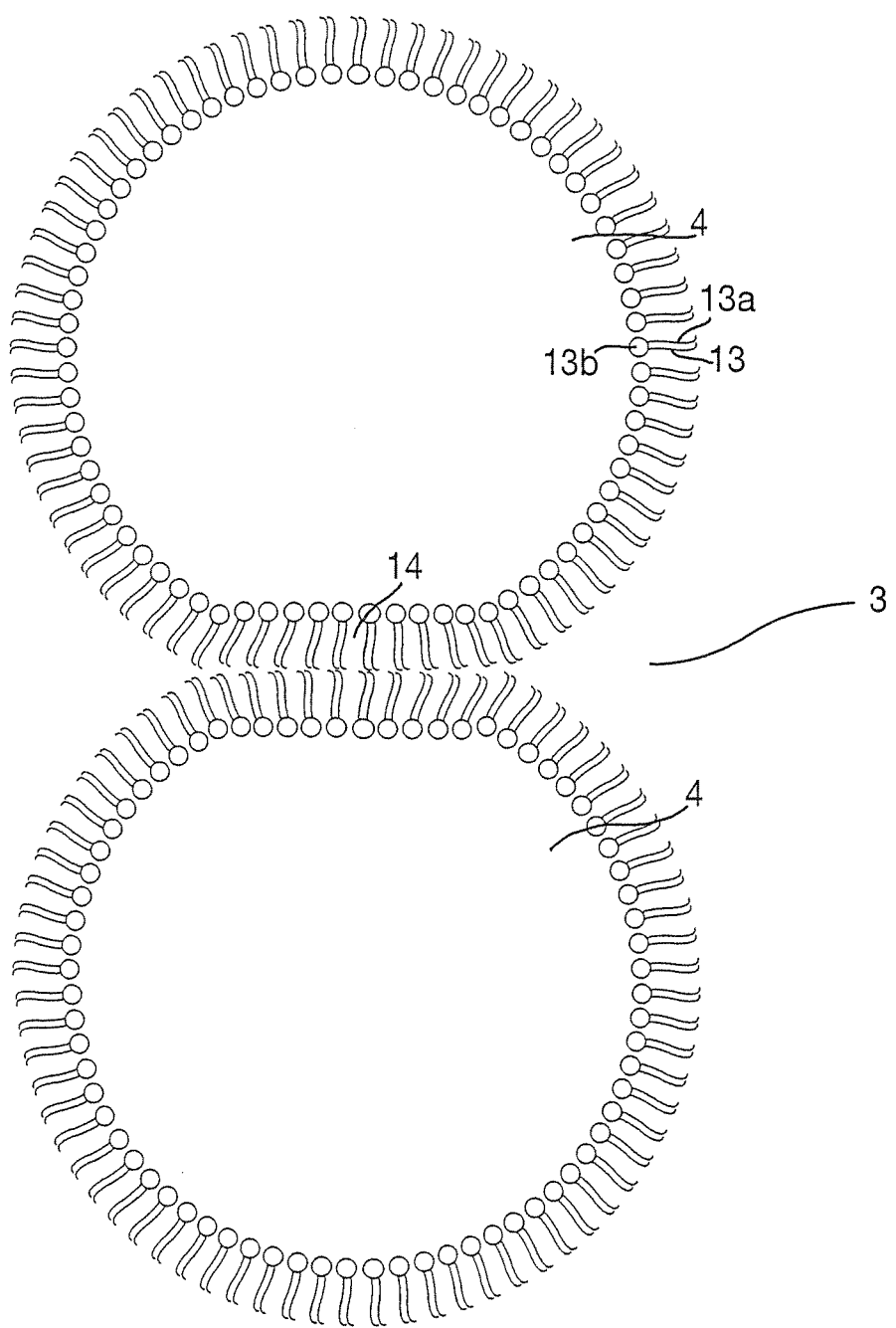
FIG. 2 is a schematic cross-sectional view of two contacting droplets with a bilayer formed as an interface therebetween.

An apparatus 1 which is suitable for handling droplets of aqueous solution to perform the present method is shown in FIG. 1. The apparatus 1 comprises a container 2 being a 1 mL Perspex bath. The container 2 contains an oil 3.

Within the oil 3 are two droplets 4 of aqueous solution. As the oil 3 is a hydrophobic medium, the aqueous solution of the droplets 4 does not mix with the oil 3 to any large extent. Some mutual solubility is expected depending on the solubility limit of a hydrocarbon in the water and the water in the hydrocarbon. The droplets 4 are formed into the oil 3 simply by dispensing the aqueous solution, for example from a conventional pipette or indeed any suitable dispenser. The dispenser is preferably of a type which allows the volume of the droplets 4 to be controlled. Experiments have been performed using droplets 4 of volume in the range from 200 nL to 800 nL but this is not limitative. One of the advantages of the method is the ability to use droplets 4 of small volume and it is expected that volumes less than 200 nL could be used. Micropipette manipulation has been used to make droplets 4 of only tens of micrometers and it is anticipated that emulsification techniques can produce suspensions of bilayer contacting droplets that have diameters of order 100 nm.

On the base of the container 2 within the oil 3, the apparatus 1 is provided with three supports 5 having a hydrophobic outer surface. The supports 5 are in this example simply 10 µL disposable pipette tips mounted on the container 1. Thus the supports 5 are annular. The droplets 4 may be disposed on the supports 5 by dispensing them in this location. By way of example, FIG. 1 shows a droplet 4-A supported on one of the supports 5. The hydrophobic nature of the outer surface of the support 5 which arises due to the support 5 being made of plastic prevents the droplet 4-A supported thereon from flowing down over the support 5. As an alternative there could be used a support in the form of a dimpled surface.

Each support 5 is provided with an anchor 6 formed by a hydrogel droplet 7 held on the end of an electrode 8 formed by a 100 µm diameter rod coated with Ag/AgCl which protrudes 0.5 mm through the aperture in the centre of the support 5 so that the hydrogel droplet 7 is disposed inside the droplet 4-A of aqueous solution. In particular the hydrogel is 5% (w/v) agarose in buffer solution. Due to hydrogel having a very high water content, the outer surface of the hydrogel droplet 7 is hydrophilic. As a result the hydrogel droplet 7 anchors the droplet 4-A supported on the support 5 because of the attraction to the aqueous solution of the droplet 4-A. In this way, the anchor 6 assists in holding the droplet 4-A on the support 5.

Further droplets 4, for example the droplet 4-B shown in FIG. 1, may be moved around within the oil 3 using a micromanipulator 9 which is shown schematically in FIG. 1 and may be of a conventional type. The droplet 4-B is held by an anchor 10 connected to the micromanipulator 9. The anchor 10 comprises a section of Ag wire which has been partially melted at the end to form a 200 µm diameter ball. This was first treated with NaClO to create an Ag/AgCl electrode 12 and then coated with a layer of hydrogel to form a hydrogel droplet 11. In particular the hydrogel is 5% (w/v) agarose in buffer solution and has a thickness of order 200 µm. Due to hydrogel having a very high water content, the outer surface of the hydrogel droplet 11 is hydrophilic. As a result the hydrogel droplet 11 anchors the droplet 4-B on the anchor 10 because of the attraction to the aqueous solution of the droplet 4-B. Thus the droplet 4-B may be moved around by controlling the micromanipulator 9 to move the anchor 10.

After the droplets 4 of aqueous solution are formed in the oil 3, a layer of amphipathic molecules, such as lipid molecules, are formed around the surfaces of the droplets 4. There are two options for achieving this.

The first option is to provide the amphipathic molecules in the oil 3. This may be done before dispensing the droplets 4 into the oil 3, that is by providing the oil 3 as a solution of the amphipathic molecules in the oil 3. Alternatively, the amphipathic molecules could be provided after dispensing the droplets 4 into the oil 3 but in that case it is harder to mix the amphipathic molecules with the oil 3. The droplets 4 themselves may contain the surfactant or the lipid in solution, micellar suspension or as lipid vesicles or liposomes.

Subsequently, after the amphipathic molecules have been provided in the oil 3 and after dispensing the droplets 4 into the oil 3, a layer of amphipathic molecules forms around the outer surface of the droplets 4 spontaneously. This can be achieved simply by leaving the droplets 4 in the oil 3 for a sufficient period of time. It is not necessary to take any special measures to encourage formation of the layer, but measures such as agitation might speed up the process.

The second option is to provide the amphipathic molecules in the aqueous solution dispensed into the oil 3 to form the droplets 4. For example, the amphipathic molecules may be provided as vesicles suspended in the aqueous solution. Subsequently, the layer of amphipathic molecules forms around the outer surface of the droplets 4 spontaneously. This can be achieved simply by leaving the droplets 4 in the oil 3 for a sufficient period of time. It is not necessary to take any special measures to encourage formation of the layer, but measures such as agitation might speed up the process.

The period of time required to form the layer of amphipathic molecules depends on the nature of the oil 3, the amphipathic molecules and the aqueous solution, but is typically of the order of tens of minutes. The required time is easily determined experimentally for any given material system. That is to say, trials can be performed in which droplets 4 are formed and left for different periods of time before the droplets 4 are brought together to form a bilayer as described below. Trials where the period of time is too short will not result in a stable bilayer so instead the droplets 4 merge together to form a larger droplet. The period of time in respect of the trials where a stable bilayer does form is the appropriate period for the material system in question.

After the layer of amphipathic molecules has formed around the droplets 4, the droplets 4 are brought into contact with one another. This is achieved in the apparatus of FIG. 1 by moving the droplet 4-B using the micromanipulator 9 until it is in contact with the static droplet 4-A supported on the support 5.

When the droplets 4 are brought into contact a bilayer of the amphipathic molecules forms as the interface between the droplets 4. This is illustrated in FIG. 2 which shows two droplets 4 of aqueous solution in the oil 3. Each droplet 4 is surrounded by a layer of amphipathic molecules 13 which are shown schematically (and not to scale) oriented with their hydrophobic tails 13a facing outwards and their hydrophilic heads 13b facing inwards. Where the droplets 4 come into contact, the layers of amphipathic molecules 13 of each droplet 4 form a bilayer 14. As it is the shape of lowest free surface energy, the bilayer 14 is planar, at least as compared to the monolayer of amphipathic molecules 13 around the remainder of the droplets 4 (the bilayer 14 may have some small degree of curvature).

The formation of the bilayer occurs spontaneously when the droplets 4 come into contact and may be observed visually through a microscope. As the droplets 4 come into contact there is a short delay where the droplet 4 deform and then spontaneously the bilayer 14 forms with a planar shape as shown in FIG. 2. The delay is the time taken for the oil 3 between the droplets 4 to be displaced out of the interface.

The formation of the bilayer 14 can also be observed by electrical measurements, in particular of the capacitance between the droplets 4. To measure this and perform other electrical measurements, the apparatus 1 further includes a circuit 15 of the same type as used in known apparatuses for studying bilayers using the conventional method described above using an aperture in a barrier. The circuit 15 is connected to the electrodes 8 and 12. An electrical contact with the aqueous solution of the droplets 4 is made due to the conductive nature of the hydrogel droplets 7 and 11. When a bilayer 14 forms, the capacitance measured by the circuit 15 increases in the same manner as with a bilayer formed by the conventional method.

A particular advantage of the present method is that the area of the bilayer 14 can be varied by moving the contacting droplets away and towards each other. In the apparatus 1 of FIG. 1, this is achieved by movement of the droplet 4-B by the micromanipulator 9. The changing area of the bilayer 14 can be observed both visually and from the capacitance measurements. In experiments the average diameter of the bilayer 14 has been changed in the range from 30 µm to 1000 µm although this is not limitative. Capacitance measurement also allows for precise control of the area of the bilayer 14 which can provide the advantage that a given experiment can be standardised by using a bilayer 14 of standard area. Another advantage of varying the area is that insertion of a membrane protein can be encouraged by initially forming a large bilayer 14 and after insertion the area of the bilayer 14 can be reduced. It has been observed that during reduction of the area of the bilayer 14, the membrane protein remains inserted, as observed by measurements, until just before the bilayer 14 separates. Such reduction in the area of the bilayer 14 can also reduce noise in electrical measurements.

It has also been observed that the bilayer 14 can be repeatedly and reliably separated by separating the droplets 4 and re-created by bringing the droplets 4 back into contact. This is advantageous as it allows complex experiments to be performed.

The apparatus 1 is convenient but in general droplets 4 of aqueous solution can be brought together to form a bilayer 14 in a wide range of apparatuses. The droplets 4 themselves are sufficiently robust to be manipulated in a number of different ways, for example by being physically pushed or placed, instead of anchoring them to an anchor. Similarly, the formation of the bilayer 14 is robust and repeatable not dependent on how the droplets 4 are manipulated. Thus a variety of different apparatuses can be used depending on the application. The manipulation technique may be very simple. For example, the droplets 4 may be moved simply by pushing them using a simple probe such as a glass or plastic rod. Alternatively, more complex manipulation techniques may be applied. For example the droplets may be moved using micro-fluidic apparatus. There is extensive discussion in the literature of micro-fluidics being used to move droplets of aqueous solution in oil and such techniques may be advantageously applied to the present invention, for example to facilitate high through-put screening.

A simple, alternative apparatus 16 which has been used is shown in FIG. 3. In this case, the base of the container 2, which in this case is made of teflon, has electrodes 17 protruding through the base. The droplets 4 are supported on the base enveloping the electrodes 17. The droplets 4 are positioned simply by dispensing them in the oil 3 and subsequently manipulated by pushing them around. For example, droplets 4 may be dispensed onto the electrodes 17 or may be dispensed to a different area of the base and pushed onto the electrodes 17. Although the apparatus 1 of FIG. 1 is more convenient to use, the apparatus 16 of FIG. 3 does allow bilayers 14 to be formed and monitored, thus demonstrating the robustness of the technique.

Conversely it is anticipated that other more complicated apparatuses could be used, depending on the application. For example for use in screening, an array of droplets 4 might be supported and one or an array of further droplets 4 might be moved relative thereto. Another possible way to move the droplets 4 would be to use micro-fluidics equipment or electrical patterned equipment.

As already discussed, the bilayers 14 formed by the present method may be used to perform a wide range of experiments involving a process occurring at or through the bilayer of the amphipathic molecules. Some examples of actual experiments which have been performed to demonstrate the efficacy of the present method are given below.

For example, having established that droplets 4 adhere and form a bilayer 14 at the contact zone, it is of interest to measure the water permeability of the bilayer 14 such as in the GMO/solvent bilayer system. This easily accomplished by simply forming two droplets 4 each droplet 4 having different osmotic pressure. In the experiment carried out, we chose to assemble one droplet 4 of solution of 500 mOsm glucose and the other droplet 4 of pure deionized water. The two micropipettes that form the droplets 4 are filled each with the different solution, and using the pressure control, positive pressure is applied to first one and then the other to generate the two droplets 4. Forming the droplets 4 in GMO-squalene ensures that water is not rapidly lost to the surrounding hydrocarbon phase and that changes in volume of the droplets 4 represents the passage of water from the water droplet 4 to the glucose solution droplet 4 down the osmotic gradient, through the bilayer 14 formed at the contact. The experiment is then to simply assemble the droplets 4 in to adherent contact and record on video their progress and volume changes (calculated from the diameters) that occur due to water transport. The glucose solution droplet 4 takes up the water from the pure water droplet 4 and grows as the water droplet 4 shrinks Data is then plotted as droplet volume with time.

In many types of experiment, the physical process is monitored by taking electrical measurements, eg of capacitance, current or voltage, using the circuit 15 in a similar manner to known techniques. To this end, the circuit 15 may, by way of example, comprise a patch-clamp amplifier (Axopatch 200B; Axon Instruments), filtered with a low-pass Bessel filter (80 dB/decade) with a corner frequency of 2 kHz and then digitized with a DigiData 1320 A/D converter (Axon Instruments) at a sampling frequency of 5 kHz. The container 1 and amplifying headstage of the circuit 15 may be enclosed in a metal box to serve as a Faraday cage.

By way of example, the electrical measurement may measure the current representative of the passage of ions through a membrane protein which is an ion channel. However, it is not essential to use electrical measurements, as any measurement characterising the process in question may be used. One alternative to electrical measurement is optical measurement, for example of a fluorescent molecule which is transported across the bilayer 14 or which responds to another molecule transported across the bilayer 14 or to the potential across the bilayer 14.

Many experimental techniques involve the insertion of a membrane protein into the bilayer 14, the process under study relating to the function of the membrane protein. In this case, the membrane protein may be used by providing it in the aqueous solution of one or more of the droplets 4. The membrane protein then inserts spontaneously into the bilayer 14. This can be achieved simply by leaving the bilayer 14 until insertion occurs without taking any special measures.

Above, only a single bilayer 14 between two droplets 4 has been considered. However, it is a particular advantage of the present method that more than two droplets 4 may be brought into contact to form plural bilayers 14 between the contacting droplets 4. The droplets 4 may be arranged in a chain or network. For example, in the apparatus 1 of FIG. 1, three droplets 4 may be arranged on the three supports 5 with the droplets 4 contacting each other in a chain, or alternatively droplets 4 on the three supports 5 may be interconnected by other droplets 4 to form a longer chain. Such chains of droplets may be branched by connecting further droplets 4 to the chain. Branches of droplets 4 may be connected to other droplets 4 to form a network. It would be straightforward to expand the apparatus 1 of FIG. 1 or indeed any apparatus to accommodate large numbers of droplets 4 and more electrodes. Similarly in microfluidic channels two or more droplets 4 can be conjoined to make a chain, or positioned in a network pattern of channels.

As the present method of forming bilayers 14 between droplets 4 is reliable and highly repeatable, this opens up the possibility of forming and studying complex systems of droplets 4 with bilayers 14 in between which would in practical terms be prohibitively difficult to do with the conventional method of forming bilayers across an aperture in a barrier. Furthermore, multiple interactions could be studied in sequence or in parallel. The possibilities are wide-ranging and exciting, and include modelling of tissues such as heart tissue or any monolayer of epithelia, such as might exist in the gut, or retina, or ear where gap junctions provide cell to cell communication and redistribution of ions. Also, endothelial monolayers could be modelled.

Another possibility is for the aqueous solution of the droplets 4 to include solutes which cause transport through the membrane proteins, being either primary or secondary transport. In this way, the system may be self-powered. Alternatively, the system may be externally powered, for example electrically by the circuit 15 or optically with light activated systems.

To illustrate the efficacy of the present method there will now be described some experiments which have been performed using the apparatus 1 of FIG. 1.

The first experiment demonstrates that ion-conducting membrane proteins insert in the bilayer 14 allowing measurements of ionic current to be performed when a potential is applied across the bilayer 14.

In particular, two 200 nL droplets 4 were arranged on the support 5 and on the anchor 10, in both which the electrodes 8 and 12 were made of Ag/AgCl. The oil 3 was hexadecane (Sigma) and the lipid 1,2-diphytanoyl-sn-glycero-3-[phospho-rac-(1-glycerol)] (DPhPC, Avanti) was dissolved therein to form a 10 mM solution.

One droplet 4 contained an aqueous solution of 10 pg/ml wild-type (WT) staphylococcal α-hemolysin (αHL) heptamer in 10 mM MOPS, 1 M KCl, pH 7.0, while the other contained an aqueous solution of 10 μM γ-cyclodextrin (γCD, Sigma) also in 10 mM MOPS, 1 M KCl, pH 7.0. The γCD binds to WT αHL and serves as a reversible blocker, which acts as a diagnostic to show that increases in current during an applied potential are due to pore insertion rather than current leakage through the droplet/droplet interface.

With this material system, it was found that the time required for the layer of lipid to form around the droplets 4 was about 30 minutes, i.e. even though lipid is expected to be adsorbed relatively quickly upon formation of the water-oil interface, it takes about 30 minutes to establish the relatively highly dense monolayer required for bilayer formation, a density on the order of 60 Å$^2$ per molecule for this particular lipid. If the droplets 4 were kept separated for this time and then brought into contact, a bilayer 14 formed but if the droplets were left for a lesser time, the bilayer 14 was not stable and the droplets 4 merged in less than one minute after being brought into contact.

Figure 4:
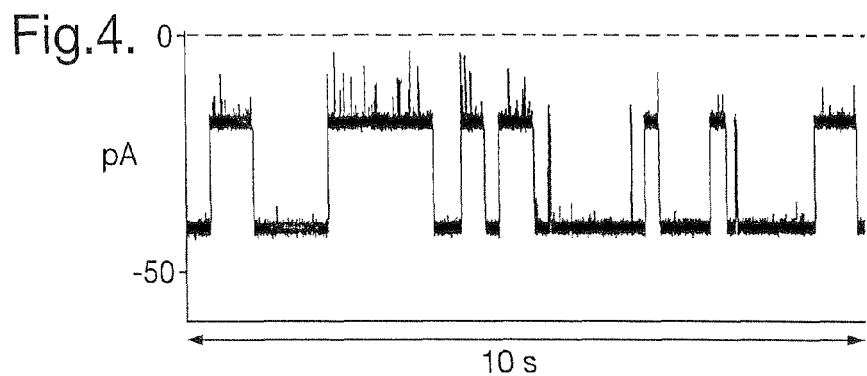
FIGS. 4 to 7 are traces of the ionic current in particular experiments performed using bilayers formed between two droplets.

After formation of the bilayer 14, αHL pores inserted therein. The time required for bilayer formation (monitored by capacitance measurements) was between five and ten minutes. The ionic current was measured, an example being shown in the trace of FIG. 4. The conductance of a single αHL pore was 798±70 pS (n=6) at −50 mV, similar to a previously reported value of 775 pS (5 mM HEPES, 1 M KCl, pH 7.4). The current was transiently attenuated by γCD binding. The residence time ($t_{off}$) for γCD bound to the αHL pore was 495±51 ms (n=4) and was similar to the residence time ($t_{off}$=421±22 ms, n=4) found in control experiments using a folded planar bilayer under the same solution conditions.

The form of the signal and the measurements demonstrate that the function of the membrane protein in the bilayer 14 is indistinguishable from those derived from a planar bilayer formed by the conventional method. In contrast the bilayer 14 had a much greater lifetime, routinely lasting several days.

The spacing between the droplets 4 was controlled by movement of the micromanipulator 9. After formation of the bilayer 14, moving the droplets 4 closer together causes the area of the bilayer 14 to expand, while moving the droplets 4 apart causes the area of the bilayer 14 to shrink. Although the bilayer 14 was thin enough (<5 nm) to accommodate protein insertion, it was so stable that single channel recording was possible even as the droplets 4 were pushed together or pulled apart, this probably being a consequence of the relatively large negative free energy of formation for this structure in this solvent-lipid system.

It was also demonstrated that the droplets 4 could be connected and disconnected repeatedly, allowing examination of a protein-containing droplet 4 many times before loss of protein activity. As an example of this, a droplet 4-A containing WT αHL was screened against an array of three analyte-containing droplets 4-B, of which: a first droplet 4 contained only buffer (10 mM MOPS, 1 M KCl, pH 7.0), the second droplet 4 contained 50 μM γCD in buffer, and the third droplet 4 contained 50 μM TRIMEB (a permethylated βCD) in buffer. The droplet 4-A containing WT αHL was placed on the movable cis electrode 12 supported by the micromanipulator 9 while the trans electrode 8 was common to the three analyte droplets 4-B, each of which was placed on one of the supports 5.

The droplet 4-A containing WT αHL was connected to the first droplet 4-B and an electrical recording was taken. Pore insertion was manifested as stepwise increases in ionic current. After recording, the droplet 4-A containing WT αHL was disconnected from the first droplet 4-B and moved to the second droplet 4-B, and another recording performed and so on. The transient binding of γCD (second droplet 4-B) to an αHL pore blocked around 60% of the ionic current, while the binding of TRIMEB (third droplet 4-B) blocked αHL almost completely. These results show repeated use of the droplet 4-A containing WT αHL. Furthermore after recording from the third droplet 4-B, the droplet 4-A containing WT αHL was reconnected to the first droplet 4-B and a final recording was taken. The αHL behaviour was identical to the behaviour shown in the first scan, demonstrating that the WT αHL sample had not been contaminated by either of the blocking analytes.

Typically, WT αHL monomer is generated by coupled in vitro transcription and translation (IVTT) by using an *E. coli* S30 extract. The protein is then oligomerized on red blood cell membranes and purified by gel electrophoresis. Since droplets under other circumstances can serve as nanoreactors, this idea was used to run the IVTT reaction directly inside a droplet 4.

In particular, using the apparatus 1 of FIG. 1 two droplets 4 were brought together. The first droplet 4 contained an IVTT mix expressing WT αHL, while the second droplet 4 contained 10 μM γCD in 2.5 mM MOPS, 250 mM KCl, pH 7.0. Although the IVTT reaction is usually performed at KCl concentrations of less than 50 mM (Promega, TB129), 250 mM KCl was added to the IVTT mix to aid in the ionic current recordings.

Figure 5:
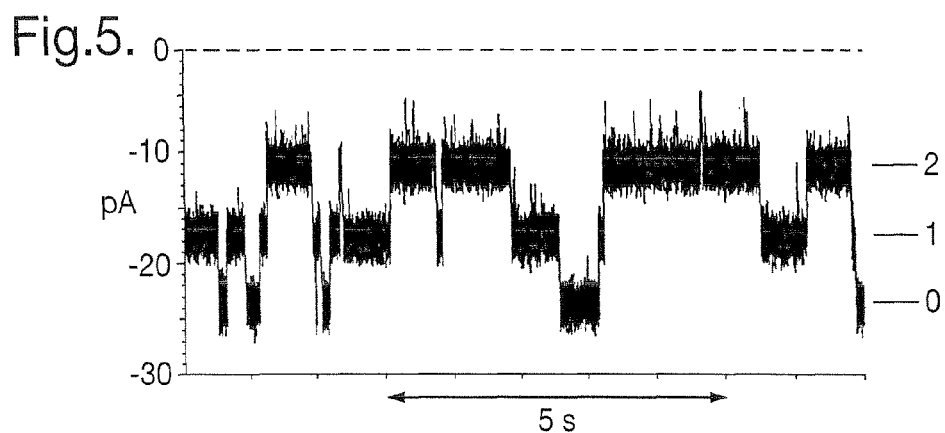

In the experiments two αHL pores inserted into the bilayer. This was observed by the characteristic increases in the ionic current at −50 mV and by γCD binding as shown in the example trace of FIG. 5 in which current levels 0, 1 and 2 show, respectively, both pores open: one pore open and one pore partially blocked by γCD; and both pores partially blocked by γCD. There is at least a two minute lag time between the mixing of IVTT components and completion of the αHL polypeptide chains. Since the droplets were placed into the oil 3 within one minute of adding the final IVTT component, the proteins must have been produced within the first droplet 4.

From an electrical perspective, the bilayer 14 and a pore inserted therein are components of a circuit, in which the bilayer 14 is a capacitor, the pore is a high-resistance conductor and the ionic solution is a wire that connects the two elements to a voltage supply. This can be used to establish the basis for more complex bio-nano-circuitry by assembling droplets 4. An example of this is now described.

Three droplets 4 were brought together in a chain, with the electrodes in the terminal droplets. The first droplet 4 contained 10 mM MOPS, 1 M KCl, pH 7.0. the second (centre) droplet 4 contained WT αHL heptamer in MOPS buffer. The third droplet 4 contained 10 μM γCD in MOPS buffer. The first and third droplets 4-A were arranged on the cis and trans electrodes respectively on a support 5, while the second droplet 4-A was held with the micromanipulator 9.

Figure 6:
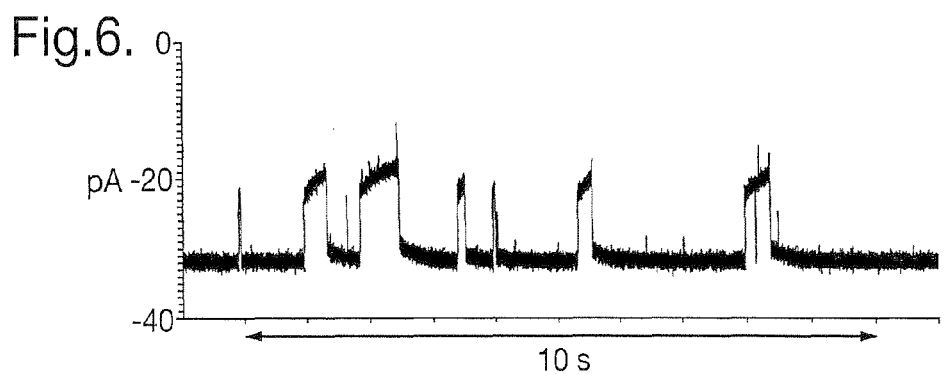

After formation of two bilayers 14 one between the first and second droplets 4 and the other between the second and third droplets 4, the ionic current was monitored and was observed only after at least one protein had inserted into each bilayer 14. However, since the formation of each bilayer 14 occurred independently, it is likely that the bilayer 14 which formed first began to incorporate pores before the second bilayer 14 formed. A example current trace, which shows the binding of γCD to the pores at the second bilayer 14, is shown in FIG. 6

The electrical properties of αHL pores and planar bilayers have been extensively studied and are straightforward to simulate in a computer model. In a single bilayer system, the γCD binding caused a sharp attenuation of current. However, when the γCD bound to an αHL pore at the interface of the double bilayer system, both the binding and release were followed by slow current shifts to the expected levels (note the curvature in the current trace of FIG. 6 immediately following binding and release of γCD). A simulation of this bio-nano-circuit also predicted this type of binding behaviour. From the model, we attribute the slow current changes as follows. The resistance of the pore at the second bilayer 14 increased when the γCD bound, which lowered the potential across the first bilayer 14. This in turn caused the first bilayer 14 (capacitor) to release some of its stored charge. Upon γCD release, this process was reversed. Our results suggest that the behaviour of chains and networks of droplets 4 is governed by basic electrical principles and are straightforward to predict. Therefore, one might engineer circuits to have specific functions, such as feedback loops.

The ability to interconnect stable, compartmentalized and communicating nanoliter volumes, or even picoliter volumes, using protein gateways forms the basis for the creation of a rudimentary artificial cell. Just as living cells carry out the functions of life in separate compartments, small networks of droplets 4 might be designed to mimic these processes. Also, just as single cells carry out functions and conjoined cells create tissue, this concept could be extended to include epithelial and endothelial monolayers of droplet cells, where even the size scale of 10 μm per cell is matched, allowing diffusive distances to be equivalent. This is important because times for diffusive processes are governed by a square relationship to distance, and so droplets 4 of diameter 100 μm would have diffusion times that are 100 times longer than droplets 4 of diameter 10 μm.

The αHL protein is an excellent starting point, since the properties of the pore, such as conductivity, ion selectivity, gating and blocking, and selective transport of small molecules can be tailored through genetic engineering. Further, αHL adopts a known orientation in the membrane, meaning that the direction of a chemical gradient can be controlled through the arrangement of the droplets 4 in a network.

An ionic gradient might be combined with ion selective pores to generate a transmembrane potential and current across one droplet interface, which in turn could be used to power processes occurring at a bilayer 14 farther along a chain of droplets 4.

The latter concept was demonstrated using a chain of three droplets. The first droplet 4 contained N123R αHL homoheptamer (in 10 mM HEPES, 100 mM NaCl, pH 7.5) which is anion selective. The second (centre) droplet 4 contained 10 mM HEPES, 1 M NaCl, pH 7.5. The third droplet 4 contained 10 μM βCD and M113F/K147N αHL homoheptamer in 10 mM HEPES, 1 M NaCl, pH 7.5 buffer. The first and third droplets 4 were connected electrically to the electrodes.

Figure 7:
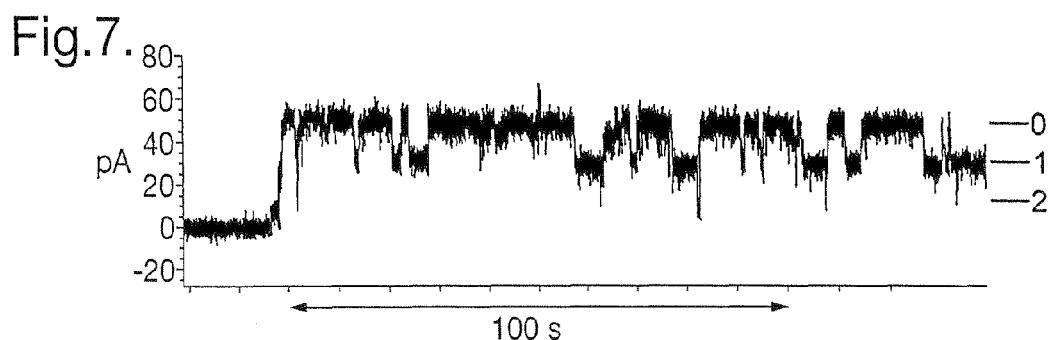

After formation of two bilayers 14 one between the first and second droplets 4 and the other between the second and third droplets 4, the ionic current was monitored. The ionic gradient across the first bilayer 14 generated a potential, while the insertion of pores at both bilayers 14 allowed this potential to be dissipated as ionic current. The selectivity of the N123R pores preferentially allowed the flow of Cl− ions from the first droplet 4 to the second droplet 4, which resulted in a positive potential at first bilayer 14. It should be noted that the circuit 15 was not used to apply a potential, rather it was only used to record the current. As shown in the example trace of FIG. 7, the power supplied by the battery effectively formed by the first and second droplets 4 enabled the observation of blocking events at the second bilayer 14, where the M113F/K147N pores reversibly bound the molecular adapter βCD The droplets 4 may be used to create simulated biosystems. It has been shown that a bilayer 14 spontaneously forms and lasts several days, which might allow slow processes, such as a complete metabolic cycle, to be studied. Proteins can be produced in situ (by IVTT) and studied by single-channel recording in the same droplet 4. The ability to disconnect and reconnect droplets 4 suggests that this approach might be a powerful tool in high-throughput screening and combinatorial chemistry applications. Further, the creation of complex networks is readily accomplished by arranging droplets 4 in a pattern, the geometry of which need not be restricted to two dimensions. For example the droplets 4 could be layered in say a hexagonal ABAB or ABCABC "crystal" pattern. The chain of three droplets demonstrates the feasibility of connecting nano-compartments with functional gateways and serves as a possible starting point for mimicking the biological hierarchy.

A network of droplets has been demonstrated as follows. Droplets 4 were created using a straight 20 cm section of 1.59 mm I.D. tubing that was filled with the oil/lipid mixture and closed at one end. With the open end up, droplets 4 were pipetted into the top of the tube just under the surface of the oil and allowed to fall nearly to the bottom of the tube. The tube was then inverted, causing the droplet 4 to descend towards the open end. Just before the droplet 4 reached the opening, the tube was brought into contact with the surface of oil 3 in a container 2 which allowed the droplet 4 to land on the bottom of the container 2.

To form the network the base of the container had a Perspex surface with a square array of micromachined dimples (a miniature "egg-crate"), with a diameter of 1 mm and with a centre to centre spacing of 700 μm each dimple acting as a support for a droplet 4. Electrodes were threaded through 200 μm diameter holes that were drilled through the bottom of the dimples. The underside of the cell was sealed with UV curable glue to ensure that the oil 3 did not leak around the electrodes. All electrodes were soldered to a common wire which was connected to the amplified (as opposed to grounded) end of a patch clamp headstage.

Figure 8:
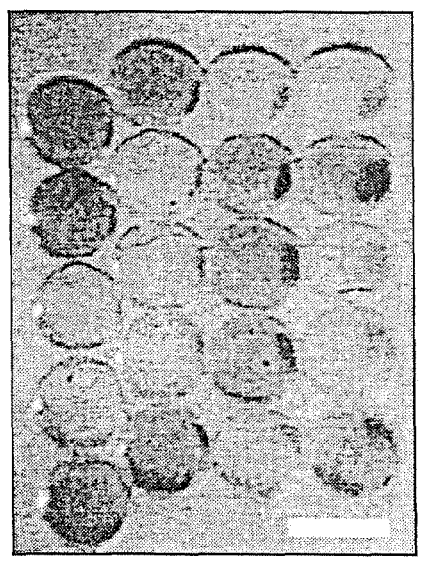
FIG. 8 is an image of a network of droplets.

For visibility, each droplet 4 contained either tetramethylrhodamine (pink) or Alexa 488 linked to a dextran polymer (yellow), in 10 mM MOPS, 1 M KCl, pH 7.0. When a droplet 4 was added, it formed a bilayer 4 with its neighbouring droplets 4 as the interstitial oil 3 was displaced. The resultant network of droplets is shown in FIG. 8.

The interface between the droplets 4 was stable to mechanical perturbation. Indeed, it was possible to puncture into a droplet 4 and then extract it by using an agarose gel-coated Ag/AgCl electrode controlled by micromanipulator. Further, it was possible to replace the missing droplet 4 by stabilizing and dropping a further droplet 4 into the empty position. This droplet spontaneously integrated into the network. Thus, component droplets of the network could be extracted and exchanged without compromising the integrity of the surrounding system.

Living tissue is differentiated into regions of specific function, which are in turn sub-differentiated into various cells. One can envision using the networks of droplets 4 in a similar fashion, with clusters of droplets 4 dedicated to certain functions. The interconnection of these clusters might eventually lead to a rudimentary artificial tissue system mimicing processes in living cells.

Membrane proteins may be incorporated, for example pores. The αHL protein pore is an excellent starting point, where the pore adopts a known orientation in the membrane, the position of protein domains (namely, the cap and stem of the pore) can be easily controlled by the arrangement of droplets 4. Further, the properties of the pore, such as unitary conductance, ion selectivity, rectification, gating, interactions with blockers and selective transport of small molecules can be tailored through genetic engineering to provide specific functions in a network.

Of immediate interest are electrically propagating systems, such as the heart. Droplets containing ion gradients, gap junctions and other proteins could be arranged in the correct order to simulate and study the mechanism of the cardiac impulse propagation. Since the droplets 4 can be disconnected and interchanged, libraries of mutant proteins could be screened using a functional network to study disease related protein irregularities. For example, an ionic gradient might be combined with an ion selective pore to generate a transmembrane potential across one bilayer 14, which in turn could be used to power processes occurring at a bilayer 14 farther along a chain of droplets 4 which has been demonstrated as discussed above.

Figure 9:
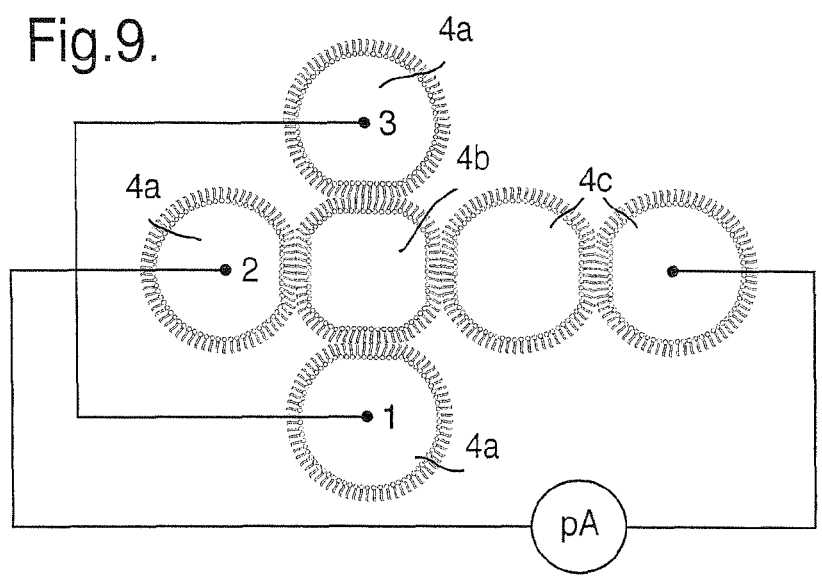
FIG. 9 is a diagram of a network of droplets forming a "bio-battery"
Figure 10:
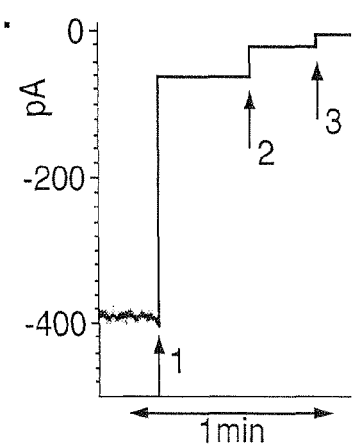
FIG. 10 is a trace of current recorded in the network of FIG. 9.

The properties of a network can be modified by changing its geometry. For example, a branched "bio-battery" was constructed as shown in FIG. 9 from six 200 nl droplets 4 using the same ionic gradient as described above. Three droplets 4a contained N123R αHL homoheptamer (in 10 mM HEPES, 100 Mm NaCl, pH 7.5) and were situated on the termini of a common branched electrode. These interfaced with three sides of an empty droplet 4b containing 10 mM HEPES, 1 M NaCl, pH 7.5, the remaining side of which droplet 4b was linked to a short chain of 10 mM HEPES, 1 M NaCl, pH 7.5 droplets 4c containing 17 ng/ml WT αHL heptamer. The opposing electrode was plugged into the terminal αHL droplet 4c. When all droplets 4a containing N123R αHL were connected with the terminal αHL droplet 4c, a high current (around −390 pA) was recorded as shown in FIG. 10. As indicated by the arrow 1, one αHL droplet 4c was then removed from the network, which caused the current to drop to around −61 pA. As indicated by the arrow 2, removal of the second αHL droplet 4a caused a further decreased in current to around −21 pA. As indicated by the arrow 3, removal of the droplet 4b stopped the current.

Nature's ability to receive and transmit information gathered from stimuli is enabled by differentiated cells working collectively. The retina, for example, senses light using rod and cone cells, which initiate a cascade of processes that transmit information down the optic nerve for interpretation by the brain. Droplet "cells" that detect light could be connected to droplet "cells" that conduct the current, much as in the retinal and retinal nerves. In fact other "senses" like taste and smell that are driven by receptor binding and channel conduction even from the hydrocarbon phase binding to receptors that are positioned in the monolayers of the droplets 4 could communicate between and within the droplet networks. Here, receptors that are probably not natural with a hydrophobic portion bounded by hydrophilic termini, would likely not partition or orient in a functional form in the droplet monolayer. But one can envision a hydrophobic domain bounded by just one hydrophilic domain that anchors the "receptor" in the monolayer facing in towards the water with the hydrophobic receptor in the oil phase. If such a molecule could be designed to respond to hydrophobic soluble molecules binding (most fragrances and active drugs are relatively hydrophobic), say by a conformational change that initiated a detectable event inside the droplet interface, then sensing of analytes ion hydrophobic solution might be possible.

Figure 11:
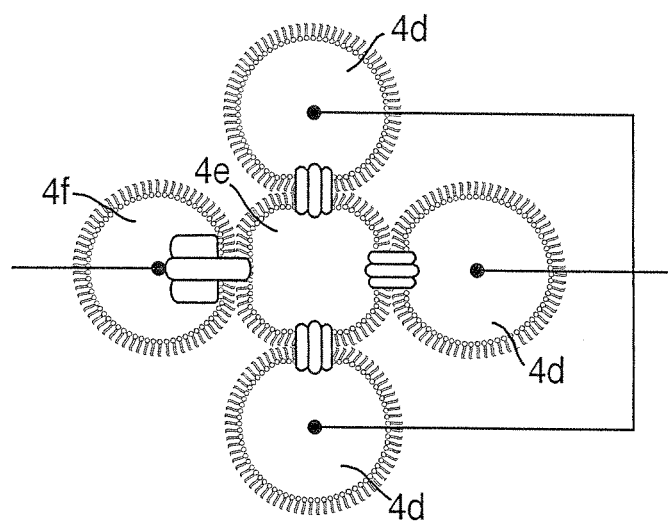
FIG. 11 is a diagram of a network of droplets having light sensing capabilities.
Figure 12:
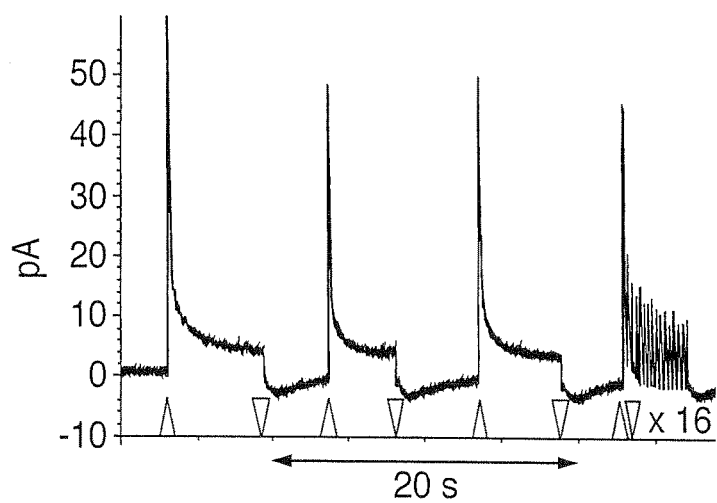
FIG. 12 is a trace of current recorded in the network of FIG. 11.

In a rudimentary mimic of the retina and optic nerve a light-sensing network was constructed based on the light-driven proton pump, bacteriorhodopsin (BR) as shown in FIG. 11. Three droplets 4d were placed on the termini of a common electrode and contained 10 mM HEPES, 100 mM NaCl, pH 7.5, 0.001% dodecylmaltoside (DDM) and 18 μM BR. A central droplet 4e contained 10 mM HEPES, 100 mM NaCl, pH 7.5, while the final outer droplet 4f contained 10 mM HEPES, 100 mM NaCl, pH 7.5 with 17 ng/ml WT αHL heptamer and had an opposing electrode plugged into it. A 1 mW green (532 nm) pen laser was used to illuminate the network. As shown in FIG. 12, when the laser was switched on, a sharp spike in current was visible, which quickly decayed to around 5 pA after 5 seconds. Switching the laser off caused the current to briefly dip to a negative value before returning to zero. Similar observations of BR behaviour have been observed using analogous systems. Three cycles of 5 seconds on and 5 seconds off were performed, followed by a rapid sequence of 16 laser pulses. Each BR transports one proton across the membrane per photon of light absorbed. Therefore, a 5 pA current suggests that tens of thousands of molecules must be functioning in the membranes 14. While such large currents might have been difficult to obtain with a single bilayer, the network of droplets 4 amplifies the light collecting ability of the system. As a control, the droplets 4 were replaced with droplets 4 containing only buffer, and the experiment was repeated. Although the electrode surfaces were exposed to the laser during illumination, no current from a photoelectric effect was observed.

In the above described experiments, the following techniques were applied.

Wild-type (WT), the M123R and M113F/K147N αHL heptamers were prepared by in vitro transcription and translation (IVTT), followed by oligomerization on red blood cell membranes. After purification by SDS-PAGE, the heptamer band was cut from the gel and the protein was extracted. Typically, αHL samples were diluted between 100 to 10,000 times in the buffer that was used to form the droplets 4. After dilution, any detergent remaining from the gel purification did not affect the stability of the bilayer 14.

Bacteriorhodopsin (BR) from *Halobacterium salinarum* was purchased from Sigma. Without purification, 1 mg of BR was solubilized by sonication for 30 minutes in 40 μl of a one to one mixture of buffer (10 mM HEPES, 100 mM NaCl, pH 7.5) and 0.01% dodecylmaltoside (DDM) in water, which yielded a dark purple suspension. When preparing BR droplets, the stock suspension of BR was diluted by a factor of 10 in 10 mM HEPES, 100 mM NaCl, pH 7.5.

The invention claimed is:

1. A droplet of aqueous solution having a volume less than 1000 nL in a hydrophobic medium, the droplet comprising a layer of amphipathic molecules around the surface of the aqueous solution, and containing a membrane protein capable of insertion into a bilayer of the amphipathic molecules.

2. A droplet according to claim 1, wherein the membrane protein is a channel or a pore.

3. A droplet according to claim 1, wherein the hydrophobic medium is an oil.

4. A droplet according to claim 3, wherein the oil is a hydrocarbon.

5. A droplet according to claim 1, wherein the amphipathic molecules are lipid molecules.

6. A droplet according to claim 1, wherein the droplet has a volume greater than 200 nL.

7. A droplet according to claim 1, wherein the droplet has a volume less than 800 nL.

8. A pair of droplets,
a first droplet of the pair of droplets being a droplet according to claim 1,
a second droplet of the pair of droplets being a droplet of aqueous solution having a volume less than 1000 nL in the hydrophobic medium, the second droplet comprising a layer of the amphipathic molecules around the surface of the aqueous solution, and
the first droplet and the second droplet being in contact with one another so that a bilayer of the amphipathic molecules is formed as an interface therebetween.

9. A pair of droplets according to claim 8, wherein the bilayer of the amphipathic molecules has a diameter in the range from 30 μm to 1000 μm.

10. A pair of droplets according to claim 8, wherein the membrane protein is a channel or a pore.

11. A pair of droplets according to claim 8, wherein the hydrophobic medium is an oil.

12. A pair of droplets according to claim 11, wherein the oil is a hydrocarbon.

13. A pair of droplets according to claim 8, wherein the amphipathic molecules are lipid molecules.

14. A pair of droplets according to claim 8, wherein the droplets each have a volume greater than 200 nL.

15. A pair of droplets according to claim 8, wherein the droplets each have a volume less than 800 nL.

16. A pair of droplets according to claim 8, wherein the second droplet contains a membrane protein capable of insertion into a bilayer of the amphipathic molecules.

17. A system comprising a bilayer of amphiphilic molecules provided at the interface between a droplet of aqueous solution having a volume less than 1000 nL in a hydrophobic medium and a further aqueous solution, wherein the bilayer contains a membrane protein.

18. A system according to claim 17, wherein the droplet comprises a layer of amphipathic molecules around the surface of the aqueous solution.

19. A droplet according to claim 17, wherein the membrane protein is a channel or a pore.

20. A droplet according to claim 17, wherein the hydrophobic medium is an oil.

21. A droplet according to claim 20, wherein the oil is a hydrocarbon.

22. A droplet according to claim 17, wherein the amphipathic molecules are lipid molecules.

23. A droplet according to claim 17, wherein the droplet has a volume greater than 200 nL.

24. A droplet according to claim 17, wherein the droplet has a volume less than 800 nL.

* * * * *